United States Patent [19]

Nunan

[11] Patent Number: 5,471,516
[45] Date of Patent: Nov. 28, 1995

[54] RADIOTHERAPY APPARATUS EQUIPPED WITH LOW DOSE LOCALIZING AND PORTAL IMAGING X-RAY SOURCE

[75] Inventor: Craig S. Nunan, deceased, late of Los Altos Hills, Calif., by Analee F. Nunan, administratrix

[73] Assignee: Varian Associates, Inc., Palo Alto, Calif.

[21] Appl. No.: 319,185

[22] Filed: Oct. 6, 1994

[51] Int. Cl.$^6$ .................................................. A61N 5/10
[52] U.S. Cl. ........................ 378/65; 378/124; 378/125
[58] Field of Search .......................... 378/64, 65, 68, 378/119, 124, 125, 126, 134

[56] References Cited

U.S. PATENT DOCUMENTS 3,582,650  6/1971  Avery .......................... 378/65
5,010,562  4/1991  Hernandez et al. .......... 378/125
5,044,006  8/1991  Cyrulnik ....................... 378/65 X
5,117,829  6/1992  Miller et al. ................. 378/65 X

OTHER PUBLICATIONS

The Stanford Medical linear Accelerator, by M. Weissbluth, C. J. Karzmark, R. E. Steele and A. H. Selby, published in vol. 72 of *Radiology*, pp. 242–253, Feb. 1959.

*Primary Examiner*—David P. Porta
*Attorney, Agent, or Firm*—Bella Fishman; David J. Power

[57] ABSTRACT

Apparatus equipped for both megavoltage radiotherapy and a diagnostic X-ray source for portal imaging. Both the high energy therapeutic and low energy diagnostic source of radiation are physically located at the same point in apparatus space, and utilize a single moveable target converter that is physically positioned according to the desired use, either therapy or diagnostics.

11 Claims, 4 Drawing Sheets

RADIOTHERAPY APPARATUS EQUIPPED WITH LOW DOSE LOCALIZING AND PORTAL IMAGING X-RAY SOURCE

FIELD OF THE INVENTION

This invention relates generally to portal imaging systems used in radiation treatment applications, and more particularly to pretreatment open field images and in-field images used in conformal radiotherapy.

BACKGROUND OF THE INVENTION

The use of linear accelerators for generation of either electron radiation or X-ray radiation is well known. In the case of electron radiation, a scattering foil and a dose chamber for measuring the electron radiation are arranged at an exit window of the accelerator, in the trajectory of the emitted electron beam. For X-ray radiation, a target for converting the electrons to X-rays, a flattening filter for broadening the X-ray beam, and a dose chamber, are arranged at the exit of tile accelerator. These systems are typically used by the medical community for treatment of cancer by radiotherapy.

One of the challenges inherent in radiotherapy treatment is the accurate positioning of the tumor in the radiation field. The main sources of the problem result from the fact that there is a natural motion of organs inside the body, which can range from approximately a millimeter in the case of the brain inside the skull to several centimeters for the organs in the trunk above the diaphragm. Another factor relates to changes which occur in the tumor over time as a result of successful treatment; as the tumor shrinks in volume, normal tissue which had been displaced returns to its original position within the treatment volume.

To accurately verify tumor positioning, portal films or electronic portal imager systems are commonly used in the radiation treatment verification process. In the case of portal imaging, the megavolt therapeutic X-rays emerging from the patient are used to generate images. However, these verification methods deliver images of low contrast and insufficient quality.

The problems associated with utilizing high energy X-rays produced by a megavolt electron beam are the result of interacting with matter primarily due to Compton scattering, in which the probability of interactions is proportional to the electron density. Low energy diagnostic X-rays, typically have energies of about 100 Kvp, where a significant portion of the interactions with matter are photoelectric, and the interactions are proportional to the cube of electron density. Tissue in the human body is typically of low density. As a result, the contrast achieved in low energy X-rays is far superior to that obtained with megavoltage X-rays, thereby allowing better distinctions of landmark features and the imaging of other features not perceptible with high energy X-rays.

One method taught in the prior art to utilize a low dose, low energy X-rays source in conjunction with a therapy X-ray source, is the external coupling of a low energy X-ray source to the accelerator's gantry head. This off-set attachment was discussed in a paper by P. J. Biggs et al. entitled "A Diagnostic X-ray Field Verification Device for a 10 Mv Linear Accelerator", *Int. J. Radiation Oncology Biol. Phys.*:ii, 635–643, 1985. This arrangement, however, has the drawback of being non-coincident with the treatment beam, thereby creating problems in applications where verification of anatomical features during a treatment sequence is advantageous, e.g. during conformal therapy.

SUMMARY OF THE INVENTION

It is an advantage of the present invention to provide a high contrast diagnostic imaging capability within the same radiation field boundaries used for administering therapy treatment.

It is a feature of the present invention to incorporate an X-ray source inside the treatment head of the accelerator to achieve a positioning of the low energy X-ray source coincident with the high energy X-ray source.

These and other advantages and features of the present invention are achieved by utilizing the existing retractable target mechanisms used in the treatment heads of linear accelerators, such as the Varian Clinac 2100 manufactured by the assignee of the present invention, which are capable of delivering both electron and X-ray radiation. The invention is also applicable to radiotherapy accelerators designed for generating only megavoltage X-rays, such as the Varian Clinac 600C.

According to the present invention, the high energy X-ray target is modified to function like a rod anode X-ray tube to include an inwardly sloped insert, having approximately a 16°–18° angle of declination, disposed at one end of the target. The water cooled actuating rod, originally coupled to the target block as part of the retraction mechanism, is replaced with a drift tube having water cooling tubes intentionally disposed along the interior side walls of the drift tube to maintain direct cooling of the target block. A compact 100 Kv electron gun is mounted to the articulating flange at the base of the retraction mechanism, with the cathode of the gun operably coupled to the upstream end of the drift tube. By engaging the actuator used in the retraction mechanism, the electron gun and drift tube assembly can be used to position the target for diagnostic imaging wherein the electron beam generated from the gun impinges the underside of the target insert to produce an angularly projected diagnostic energy X-rays collinear and coincident with a beam axis of the high energy X-ray source. Therapeutic treatment can then be resumed by repositioning the megavoltage X-ray target block in line with the trajectory of the high energy electron beam.

BRIEF DESCRIPTION OF THE DRAWINGS

FIG. 3a is an end view of the first embodiment depicting the target water-cooling tubes placed within the drift tube.

DETAILED DESCRIPTION OF THE INVENTION

For conformal radiotherapy it would be desirable to take daily pretreatment open field images of bony landmarks at orthogonal gantry angles for tumor localization and positioning in three dimensional space coordinates. It would likewise be very desirable to perform daily pretreatment in-field images at each beam/patient orientation for pretesting of the field with respect to the patient's anatomy. Without bone in the treatment field, in-field images alone are inadequate in many instances using megavoltage X-rays, regardless of dose.

Images far superior, in both contrast and spatial resolution, to present megavoltage portal images, can be obtained within acceptable dose limits for daily open field and in-field imaging, using the low current diagnostic X-ray imaging system of the present invention. By modifying the megavoltage X-ray target of a linear accelerator, such as the Clinac 2100, manufactured by the assignee of the present invention, to provide a target surface similar to that used in a rod anode X-ray tube; and incorporating a small electron gun raised to a potential of about 100 Kv into the target positioning mechanism. An electron beam generated from the electron gun and projected off the modified target surface will be collinear with the beam trajectory from the linear accelerator, with a radiation source location that is practically identical for both diagnostic and therapeutic beams, thereby allowing near diagnostic quality images within the therapy treatment field, with images that may be recorded typically by X-ray film or by electronic portal images.

Figure 1:
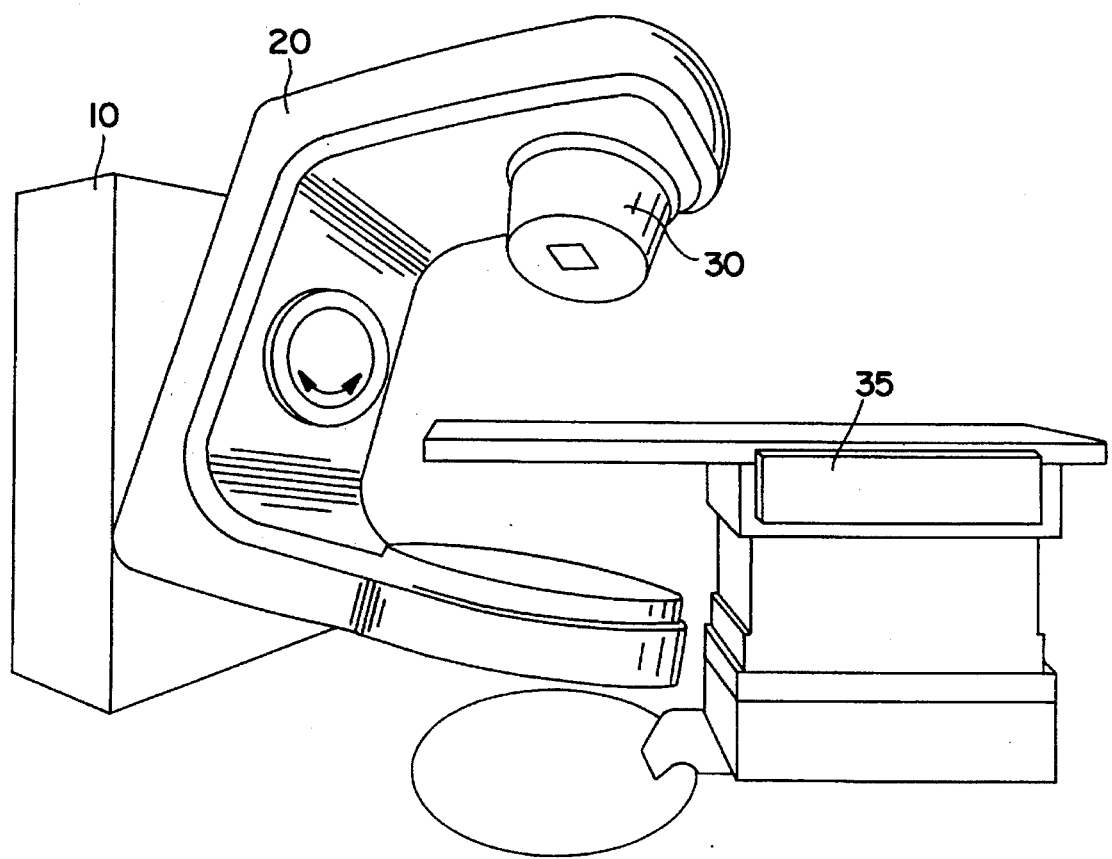
FIG. 1 is a perspective view of a conventional radiation therapy apparatus which may be modified in accordance with the present invention.

Referring now to FIG. 1, a linear accelerator of the type described above is shown, which may be capable of generating either electron radiation or X-ray radiation or both, for use in the radiotherapy treatment of patients on a treatment table 35. Stand 10 supports a gantry 20 with a treatment head 30. Next to stand 10 there is arranged a control unit (not shown) which includes operational electronics for controlling the different modes of operation of the accelerator. As it is well known in the art, a high voltage source is provided within the stand or in the gantry, to supply this voltage to an electron gun (not shown) positioned on an accelerator guide located in gantry 20. The electrons are omitted from the electron gun into the guide (not shown) for acceleration. For this purpose a HF source is utilized to supply RF(microwave) power for the generation of an electromagnetic field within the waveguide. The electrons emitted from the electron gun undergo an acceleration in the waveguide as a result of the electromagnetic field, and exit the waveguide as a high energy electron beam typically at megavoltage energies.

Figure 2:
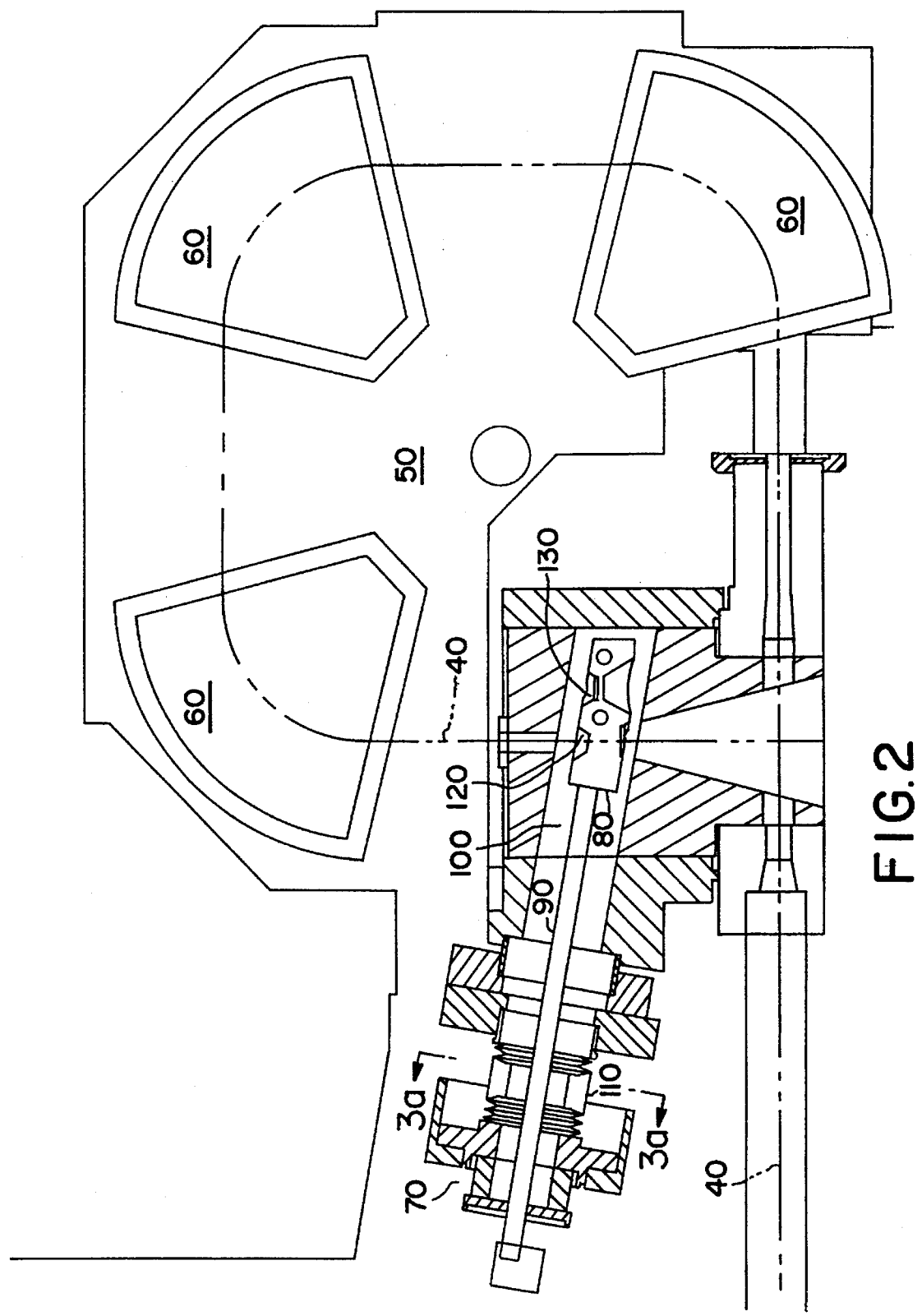
FIG. 2 is a sectional view of a conventional target retraction mechanism used in a radiotherapy apparatus such as the one depicted in FIG. 1.

Referring now to FIG. 2, a sectional view of treatment head 30 is depicted, showing electron beam 40 entering the evacuated envelope 50 where bend magnets 60 redirect electron beam 40 through 270°. Although the bend magnet is shown, it is not necessary that a magnet exist, for the purpose of this invention. Some radiotherapy accelerators utilize bend magnets, others do not. If electron radiation is to be utilized for treatment, target retraction carriage assembly 70 is used to move megavoltage target block 80 out the trajectory path of electron beam 40 by means of an actuator coupled to actuating rod 90. The actuator causes an axial movement of actuating rod 90 in direction a—a, which in turn causes megavoltage target 80, coupled to actuating rod 90 at the base of target 80, to reposition itself outside the trajectory path of electron beam 40. To ensure vacuum integrity is maintained in target cavity 100, vacuum bellows 110 is positioned to expand in direction a—a during the movement of actuating rod 90 as described. If therapeutic X-rays are required, the actuator is used as described above to reposition either target surface 120 (as depicted), or target surface 130, or other positions of megavoltage target 80, within the beam trajectory of electron beam 40, the megavolt energy level of the electron beam selected ta the accelerator. For some classes of radiotherapy accelerators, multiple treatment beam energies, both electron and X-ray are available; for others, only a single X-ray energy may be available. In the latter case, only a single target position is required for therapy.

Figure 3:
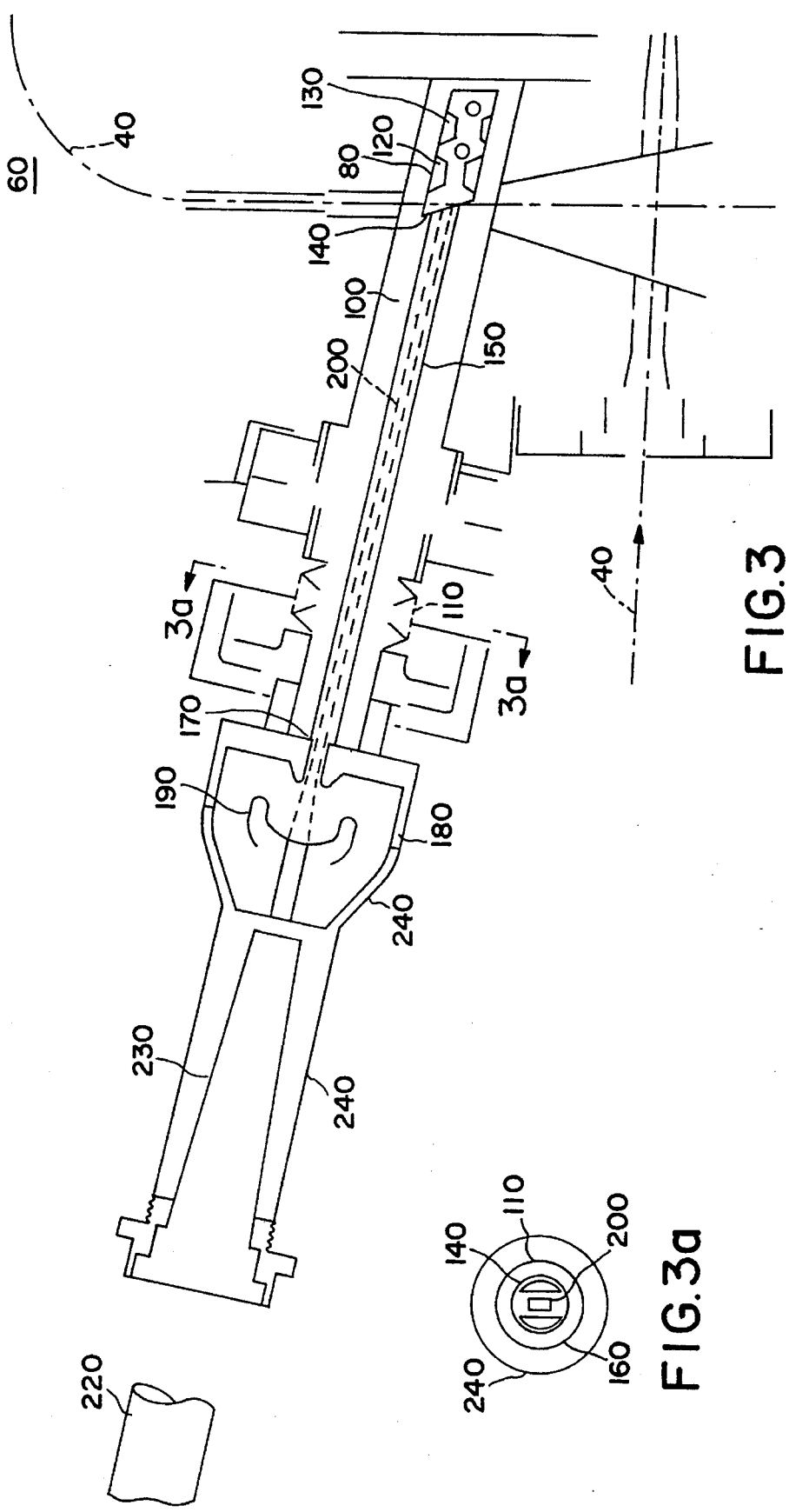
FIG. 3 is a sectional view of the first embodiment of the present invention depicting the target insert and diagnostic electron gun placement and drift tube.

In FIG. 3 the redesign of megavoltage target 80 and target carriage 70 according to a first embodiment of the present invention is shown. Target 80 is fitted at its base with high Z target face insert 140, having a declination angle of about 16° to about 18° with respect to the vertical axis of the gantry head. Actuating rod 90, in accordance with the invention, is replaced with drift tube 150 coupled to target insert 140. Disposed within drift tube 150, along the interior side walls, are water cooling tubes 160, shown in the cross sectional view depicted in FIG. 3a, for direct water cooling of target block 80.

Mounted to the flanged portion of vacuum bellows 110, and operably coupled to the upstream end 170 of drift tube 150, is a compact electron gun 180. Electron gun 180 is preferably a 50 mA gun. The gun has a cathode and focus electrode 190 shaped to deliver rectangular cross-section beam 200 of about 1.4 mm×5.0 mm on the face of target insert 140. The 50 mA electron beam 200 travels from electron gun 180 at about −100 Kv for a distance of about 16 cm, where the beam impinges on the angular face of target insert 140 to produce a diagnostic X-ray beam 210, collinear with the beam axis of electron beam 40, and having a projected focal spot of about 1.4 mm×1.4 mm located practically at the same source location as the high energy therapy beam. Utilizing a conservative estimate of $1A/cm^2$, this equates to an equivalent cathode diameter of approximately 2.5 mm. Electron gun 180 is powered by a compact high frequency type 50 mA 100 Kv voltage multiplier, which is driven by a small power source. An example of such a source is the SILO type compact high voltage power supply manufactured by the assignee of the present invention. Power is delivered to electron gun 180 by high voltage power cable 220 through tapered mating plug 230 surrounded by high voltage insulator 240.

Figure 4:
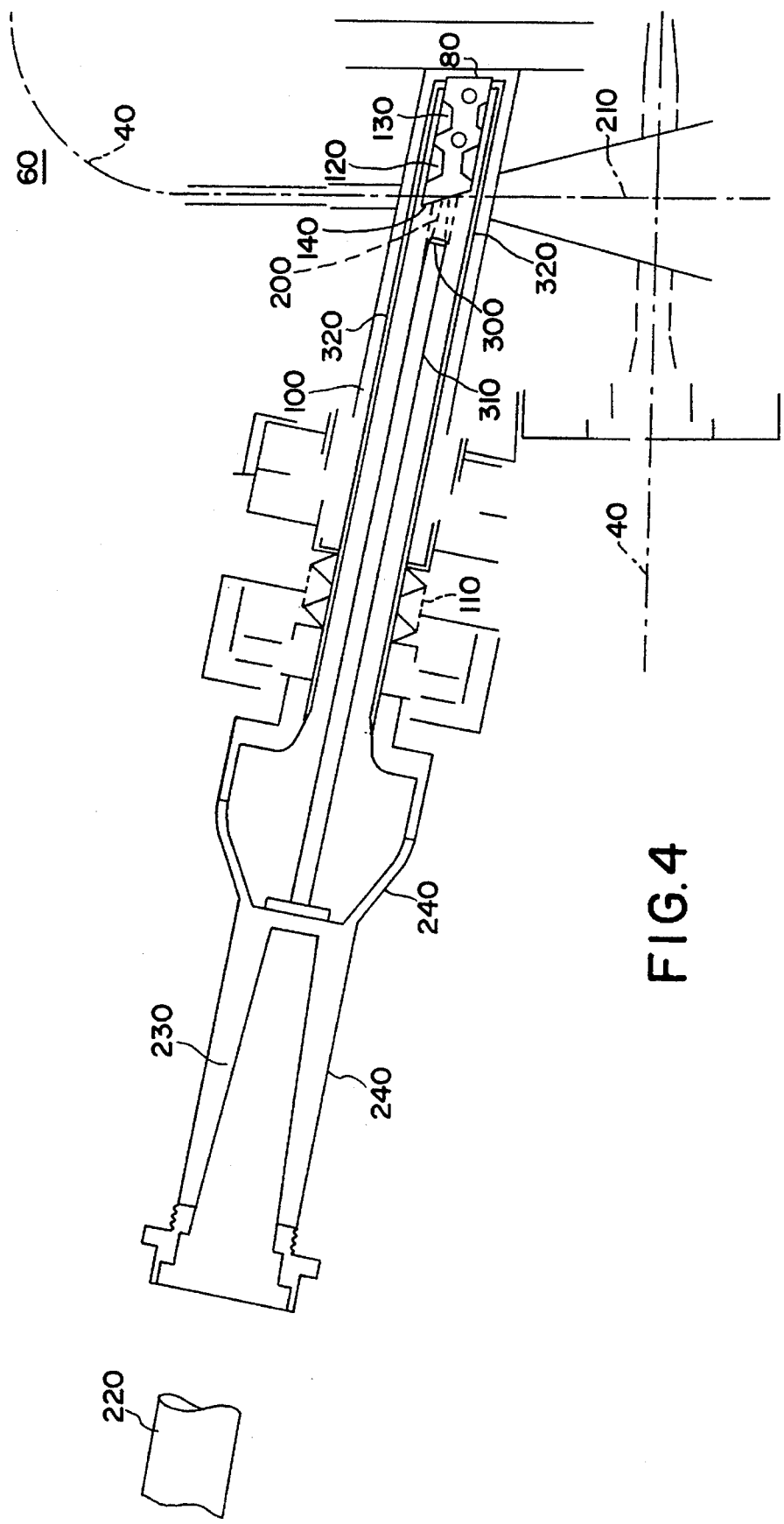
FIG. 4 is a sectional view of the second embodiment of the present invention depicting a cathode of the type used in travelling wave tubes mounted on a rod for use as an electron gun.

In an alternative embodiment, shown in FIG. 4, cathode 300 of the type typically used in travelling wave tubes, both having a micro perveance of about 0.0002, is mounted on rod 310 at about 100 Kv. Rod 300 is positioned about 10 mm from the target face of insert 140, and as in the previous embodiment emits beam 200 which impinges on the face insert 140 and produces collinear diagnostic X-ray beam 210. Like the previous embodiment, megavoltage target 80 is secured in place and directly water cooled by water cooling tubes 320, and is driven by about a −100 Kv source, with filament power being fed through a compact high voltage insulator.

For both of the above described embodiments, the ripple resulting from the high frequency cascaded transformer and power source, is similar to that obtained with a three-phase, full wave rectification type conventional X-ray source, thereby providing a high average kilovoltage.

In operation, the actuator is reconfigured and repositioned according to generally known engineering principles to accommodate the addition of the electron gun component of the invention. The actuator is then used to position the face of target insert 140 for pretreatment diagnostic imaging by aligning the target face within vacuum cavity 100 such that projected diagnostic X-ray beam 210 is axially aligned with the trajectory of electron beam 40, and therefore with the central axis 210 of the high energy treatment field. In order to minimize motion artifact and to maximize signal to noise ratio in electronic detectors, it is desirable to limit exposure time for a given patient dose. Therefore, the diagnostic X-ray source should be operated at the maximum beam current the target can tolerate, consistent with long target life. Experimental results show that a 1.4 mm×1.4 mm focal spot will have a 0.56 mm geometric penumbra at the detector when located 140 cm from the source for an object point 100 cm from the source. The penumbra fringe is within acceptable limits for a 51 cm×51 cm detector having a 512×512 pixel sensor with 1 mm×1 mm pixels, and is far superior to the 3 mm diameter focal spot generated by therapeutic megavoltage beams. To produce 1 cGy dose (1075 mR exposure) at 100 Kvp without excessive heating of target 80 the electron beam charge for the 1.4 mm×1.4 mm focal spot was found to be 130 mA/s; 30 mA for 4.3 seconds. A 0.375 cGy dose (400 mR) is likewise obtainable with 48 mA/s using 45 mA for 1.07 seconds. As a result, for operation of the present invention, a 50 mA maximum design beam current is preferred, with typical operation at 40 mA for up to 1.5 seconds (60 mA/s) at 100 Kvp to deliver up to 500 mR (0.465 cGy, 0.31 cGy/second) for daily portal imaging at a patient surface distance of 90 cm. With the diagnostic energy of 100 Kvp, the mean energy of the useful image producing primary photons penetrating the patient at about 60 Kev, the mass attenuation coefficient is 0.205 $cm^2/g$ in bone. Therefore, a 1% change in primary photon transmission is produced by 0.049 cm of muscle or 0.021 cm of bone. For 6 Mv X-rays, a 1% change in primary photon transmission requires 0.4 cm of bone. The improvement in contrast sensitivity of bone, obtained through the use of the present invention, is 0.14 cm/0.021 cm, a factor of 6.7.

Through the use of the present invention, daily pretreatment enlarged orthogonal views for patient localization can be performed, after which the megavoltage target can be repositioned or removed from the trajectory of the accelerator beam for therapeutic X-ray or electron radiation treatment. Immediately after each therapeutic irradiation, the diagnostic target position can be reinstated for verification.

The scope of this invention is not restricted to the structures shown in the drawings, but includes various modifications and variations that are adaptable to other target positioning mechanisms to provide a diagnostic X-ray beam collinear with therapeutic beams. In particular, the aspects of the invention have been described in relation to a gantry mounted target, it will be apparent that targets designed in other positions may be modified as described herein, and implemented in conjunction with an internal diagnostic source to create a diagnostic X-ray beam collinear with therapeutic beams.

What is claimed is:

1. An apparatus for generating therapeutic and diagnostic radiation for medical imaging and treatment of a treatment field, said apparatus comprises:

an accelerator, said accelerator having a first electron gun and accelerating means for producing a high energy electron beam, said beam capable of being converted to a therapeutic X-ray beam;

a movable target for conversion of electrons to X-rays, said target having a body and angular face insert disposed at one end of said body, wherein in treatment mode said target body located on a trajectory of said high energy electron beam and in diagnostic mode said target body located off the trajectory of said high energy electron beam;

means for positioning said target for diagnostic imaging and treatment; and a second electron gun for producing a low energy electron beam placed within said means for positioning said target, said low energy electron beam impinging on said target face insert and producing a diagnostic X-ray beam into said treatment field, said diagnostic X-ray beam having a central axis which is collinear and coincident with a central axis of said therapeutic beam and a central axis of said treatment field, said X-ray diagnostic and therapeutic beams having identical source coordinates.

2. The apparatus of claim 1 wherein said target face insert has a declination angle in the range of about 16° to 18° with respect to said central axis of said collinear X-ray beams.

3. The apparatus of claim 2 wherein said means for positioning further comprises a drift tube having upstream and downstream ends and interior side walls, said upstream end connected to said second electron gun and said downstream end connected to said target face insert.

4. The apparatus of claim 3 wherein said drift tube comprises water cooling tubes disposed along said interior side walls of said drift tube for direct water cooling of said target.

5. The apparatus of claim 4 wherein said first electron gun and accelerator means produce megavoltage energy electron beam.

6. The apparatus of claim 4 wherein said second electron gun produces the energy of said low energy electron beam of about 100 Kv.

7. An apparatus for generating therapeutic and diagnostic radiation for medical imaging and treatment of a treatment field, said apparatus comprises:

a movable target positioned on and off a central axis of said treatment field for operation in therapeutic and diagnostic modes respectively, said target having a body and a sloped face insert disposed at one end of said body;

means for positioning said target for medical imaging and treatment;

a high energy electron beam source for producing a therapeutic beam by converting a high energy electron beam striking said target body to X-rays;

a low energy electron beam source for producing a diagnostic beam by converting a low energy electron beam striking said sloped face insert to X-rays, said low energy electron beam source placed within said means for positioning said target, a central axis of said diagnostic beam being aligned with a central axis of said therapeutic beam, said diagnostic and therapeutic beams originating at the same source coordinates in said apparatus; and a drift tube disposed within said means for positioning said target between said low energy electron beam source and said target face insert.

8. The apparatus of claim 7 wherein said drift tube comprises water cooling tubes disposed along interior side walls of said drift tube for direct water cooling of said target.

9. A method for selectively generating therapeutic or diagnostic radiation for medical imaging or treatment of a treatment field comprising the steps of:

providing a movable target for conversion of electrons to X-rays, said target having a body and an angular face insert disposed at one end of said target body;

positioning said target for a diagnostic mode;

producing a low energy electron beam from an electron gun and power supply associated with said gun;

directing said low energy electron beam onto said angular face insert for obtaining a diagnostic X-ray beam so that said diagnostic beam being projected from said face insert onto said treatment field having a central axis coincident to a central axis of said treatment field;

producing a high energy electron beam from another electron gun and an accelerator means;

switching from said diagnostic mode to a treatment mode by interrupting said low energy electron beam;

positioning said target for said treatment mode; and directing said high energy electron beam onto said body of said target for obtaining a therapeutic X-ray beam having a central axis coincident to said central axis of said treatment field, said therapeutic X-ray beam having identical source coordinates with said diagnostic X-ray beam.

10. The method of claim 9 wherein the step of positioning said target for said diagnostic mode comprises the step of retracting said target body off said central axis of said treatment field.

11. The method of claim 9 where in the step of positioning said target for said treatment mode comprises the step of moving said target body to intercept said central axis of said treatment field.

* * * * *